(12) United States Patent
Fendrock et al.

(10) Patent No.: US 8,029,313 B2
(45) Date of Patent: Oct. 4, 2011

(54) DISPOSABLE NEEDLE ELECTRODE WITH IDENTIFICATION, AND ALTERABLE, CONNECTOR INTERFACE

(75) Inventors: Charles Fendrock, Sudbury, MA (US);
Louis J. Barbato, Franklin, MA (US);
Charlie Wu, Newton, MA (US)

(73) Assignee: NeuroMetrix, Inc., Waltham, MA (US)

( * ) Notice: Subject to any disclaimer, the term of this patent is extended or adjusted under 35 U.S.C. 154(b) by 130 days.

(21) Appl. No.: 12/274,759

(22) Filed: Nov. 20, 2008

(65) Prior Publication Data
US 2009/0253274 A1    Oct. 8, 2009

Related U.S. Application Data

(60) Provisional application No. 61/003,823, filed on Nov. 20, 2007.

(51) Int. Cl.
*H01R 3/00* (2006.01)
(52) U.S. Cl. ........................................ 439/489; 439/955
(58) Field of Classification Search .................. 439/489, 439/490, 955
See application file for complete search history.

(56) References Cited

U.S. PATENT DOCUMENTS

| | | | |
|---|---|---|---|
| 4,902,244 A * | 2/1990 | Endo et al. | 439/489 |
| 4,925,402 A * | 5/1990 | Inaba et al. | 439/490 |
| 5,169,336 A * | 12/1992 | Taguchi | 439/489 |
| 5,170,788 A | 12/1992 | Blumenfeld | |
| 5,222,164 A * | 6/1993 | Bass et al. | 385/14 |
| 5,588,873 A * | 12/1996 | Hamai et al. | 439/489 |
| 6,208,891 B1 | 3/2001 | Flower | |
| 6,655,983 B1 | 12/2003 | Ishikawa et al. | |
| 6,890,197 B2 * | 5/2005 | Liebenow | 439/188 |
| 7,314,392 B2 * | 1/2008 | Pharn et al. | 439/676 |
| 7,384,300 B1 * | 6/2008 | Salgado et al. | 439/489 |
| 2002/0169371 A1 | 11/2002 | Gilderdale | |
| 2004/0204669 A1 | 10/2004 | Hofmann | |
| 2008/0090451 A1 * | 4/2008 | Feldman | 439/490 |

* cited by examiner

*Primary Examiner* — Hae Moon Hyeon
(74) *Attorney, Agent, or Firm* — Pandiscio & Pandiscio (57) ABSTRACT

An interconnect for connecting a needle electrode to a neurological testing device, the interconnect comprising: a needle-side connector and a device-side connector, wherein the needle-side connector and the device-side connector have complementary aspects so as to ensure that the correct needle electrode is used with a given neurological testing device.

46 Claims, 7 Drawing Sheets

DISPOSABLE NEEDLE ELECTRODE WITH IDENTIFICATION, AND ALTERABLE, CONNECTOR INTERFACE

REFERENCE TO PENDING PRIOR PATENT APPLICATION

This patent application claims benefit of pending prior U.S. Provisional Patent Application Ser. No. 61/003,823, filed Nov. 20, 2007 for DISPOSABLE NEEDLE WITH IDENTIFICATION, AND ALTERABLE, INTERFACE, which patent application is hereby incorporated herein by reference.

FIELD OF THE INVENTION

This invention relates to disposable electrophysiological needles in general, and more particularly to a novel connector interface that provides the ability to identify the needle which is being connected to a neurological testing device. This invention also provides a means to mark a needle as "used" when a procedure is performed using the needle. These two features help ensure that the correct needle is used with a given neurological testing device and improves the medical safety of the needle by alerting the operator if the needle has already been used.

BACKGROUND OF THE INVENTION

Surgical procedures often require the application of peripheral nerve blocks, which generally involve injecting a patient with a local anesthetic near a nerve in order to eliminate any pain or sensation during the surgical procedure.

In addition, patients with nerve damage due to maladies such as carpal tunnel syndrome often require the injection of a drug (such as a steroid or an anesthetic) near the nerve. In this respect it should be appreciated that an estimated 40 million Americans suffer from chronic pain symptoms, with more than half of them over the age of fifty-five. And nearly 60% of all of those who suffer from diabetes also have acute peripheral neuropathy. Local anesthesia can be applied to relieve chronic or acute pain situations, with two basic techniques being used: peripheral nerve block and plexus anesthesia. As noted above, peripheral nerve block is the injection of a local anesthetic in the vicinity of a peripheral nerve so as to anesthetize the region surrounding the nerve. Plexus anesthesia is the injection of a local anesthetic in the vicinity of a network of intersecting nerves (i.e., a nerve plexus) in order to anesthetize the entire area of several or all of the nerves stemming from the plexus. Thus, regional nerve blocks and plexus anesthesia can aid patients who suffer from chronic pain such as lower back pain, neck pain, sciatica (from a herniated disc), spinal stenosis and reflex sympathetic dystrophy (a complex regional pain syndrome). In addition, regional nerve blocks and plexus anesthesia can also help those suffering from shingles, cancer and painful peripheral vascular disease.

In order to provide effective peripheral nerve blocks and plexus anesthesia, it is important to first accurately locate the nerves which are to be anesthetized. Peripheral Electrical Nerve Stimulation (PENS) can be used to accurately locate the targeted nerve. In PENS, electrical pulses are sent, via a needle electrode, into the desired nerve(s) so as to trigger depolarization of the nerve and elicit a reaction in the muscle which is innervated by the nerve. A constant current source, delivered via the needle electrode, supplies the depolarizing current to the nerve. The amount of charge received by the nerve depends on the distance between the tip of the needle and the nerve: the closer the tip is to the nerve, the greater the reaction of the muscle. Thus, by monitoring muscle reaction, the peripheral nerve can be reliably located. Once the peripheral nerve has been located, one of several anesthetics, in combination with a steroid and/or opioid, can be administered by the physician.

Needle electrodes are also used in connection with botulinum injections. More particularly, nearly three million botulinum injections are administered annually in the United States for cosmetic purposes or for therapeutic purposes (e.g., for treatment of focal dystonia, or for treatment of painful muscle spasms, etc.). The injection of the botulinum toxin is a process that takes ten to thirty minutes. A topical anesthetic is applied to the area in question for numbing purposes, and then small amounts of the botulinum toxin is injected into predetermined areas with an extremely thin needle. Needle electrodes are used to help identify the appropriate areas for the botulinum injections.

Needle electrodes are also used for electromyography (EMG) studies. More particularly, electromyography is a technique for recording and evaluating the physiological properties of muscles, and is widely used to diagnose and determine the underlying causes of most peripheral neuropathies, including carpal tunnel syndrome and radiculopathy. In electromyography, an electromyograph is used to detect the electrical potential between muscle cells while they are active and at rest. To perform intramuscular EMG, a needle electrode is inserted through the skin and into the muscle tissue. A trained medical professional observes the electrical activity while inserting the needle electrode. In intramuscular EMG, three types of signals are generally studied: (i) the electrical activity of the muscle when the needle is inserted, (ii) the electrical activity of the muscle at rest, and (iii) the electrical activity of the muscle when it is consciously contracted by the patient. Abnormal spontaneous activity of the muscle at rest, and abnormal shape, size and/or frequency of the motor unit potential of the contracted muscle, may indicate nerve and/or muscle damage.

Needle electrodes are also used in many other diagnostic and/or treatment systems.

The needle electrodes currently used for near-nerve anesthesia injections, botulinum injections, EMG applications, etc. are so-called "off-the-shelf" products, in the sense that they have a distal end which is specifically configured according to the intended use and a proximal end which can be inserted into any common cable connector so that the needle can be electrically connected to a neurological testing device. These conventional needle electrodes (which are commonly referred to in the industry as simply "needles") currently have no means for ensuring that the correct type of needle (i.e., an anesthesia needle, a botulinum needle, an EMG needle, etc.) is connected to a neurological testing device, or for ensuring that a needle has not been previously used.

By way of example but not limitation, two needle electrodes ("needles") currently commercially available are the STIMUPLEX®—a needle manufactured by B. Braun for drug therapy, and the NEUROLINE® concentric needle manufactured by AMBU® for EMG. The Braun STIMUPLEX® needle is a standard, beveled, hypodermic needle electrode which fits into any Deutsches Institut für Normung (DIN) 42802 cable connector. The Braun STIMUPLEX® needle provides a pinpoint electrode and smooth insertion as well as atraumatic puncture of the skin. The AMBU® NEUROLINE® needle is a standard, beveled, concentric needle electrode, with TEFLON insulation for electrical protection, which also fits into any DIN 42802 cable connector. The AMBU® NEUROLINE® needle provides a sharp tip for easy insertion, and an extra-smooth coating for low insertional friction. Thus it will be seen that the Braun STIMUPLEX® needle used for drug therapy differs significantly in construction from the AMBU® NEUROLINE® needle used for EMG. However, both needles fit into any DIN 42802 connector—meaning that the Braun STIMUPLEX® needle might inadvertently be used in an EMG procedure (rather than in the drug therapy procedure for which it was designed), or the AMBU® NEUROLINE® needle might inadvertently be used in a drug therapy procedure (rather than in the EMG procedure for which it was designed), etc. Neither of the foregoing needles, nor any of the other electrophysiological needles currently on the market, provides an effective or practical means for successfully ensuring that the correct needle is used with a given neurological testing device, or for prevention of its re-use.

In addition to the fact that needle constructions differ according to their intended use, there is a further reason why it may be important to be able to properly identify the needle electrode being connected to a neurological testing device. More particularly, it is anticipated that future designs of needles may incorporate special features that may dictate certain operating parameters. By way of example but not limitation, a needle may have a dielectric on the outside of the needle that requires a minimum breakdown voltage. In this situation, as well as many others, it may be important to ensure that the proper needle is being used with a given neurological testing device.

The re-use of medical needles, while not necessarily a major issue in the United States, is a serious problem in lesser-developed countries where medical resources are frequently scarce. The World Health Organization has estimated that at least half of all medical injections in 17 developing countries were administered with re-used needles, significantly contributing to the skyrocketing rate of AIDS and HIV. An effective and fail-safe means of detecting the re-use of needles would be of substantial benefit to the medical community.

There is, therefore, a need in the industry for a simple, cost-effective approach for ensuring that the proper needle electrode is used with a neurological testing device, and for detecting when a needle has been previously used.

For electrophysiological needles, the interconnect used to couple the needle electrode with the neurological testing device is a key component which is present in all systems. This key component provides an opportunity to ensure that the proper needle electrode is being used with a given neurological testing device and that the needle has not been previously used.

It is, therefore, a principal object of the present invention to provide a simple, cost-effective interconnect which can be used to quickly determine the identity of an electrophysiological needle and, optionally, detect when a needle has been previously used.

SUMMARY OF THE INVENTION

The present invention comprises a novel interconnect for connecting a needle electrode to a neurological testing device, wherein the interconnect is configured to determine if the correct needle is being connected to the neurological testing device. The invention preferably also comprises an additional, and supplementary, ability to mark the needle as "used" when a procedure is performed, thereby making it easy to determine when a needle has been previously used.

In one form of the present invention, there is provided a novel interconnect for connecting a needle electrode to a neurological testing device. The novel interconnect comprises a needle-side connector and a mating device-side connector, wherein the needle-side connector and device-side connector have complementary aspects so as to ensure that an appropriate needle electrode is used with an appropriate neurological testing device. Furthermore, the novel interconnect is preferably constructed so that the needle-side connector is marked during use, so as to facilitate determining when the needle electrode has been previously used, whereby to help ensure single use of the needle electrode.

The novel interconnect can be constructed using electrical means, optical means, and/or mechanical means. The novel interconnect is preferably constructed as two complementary parts (e.g., mating male and female parts), one of which (i.e., the needle-side connector) is attached to the needle and the other of which (i.e., the device-side connector) is attached to the neurological testing device.

Electrical means for achieving identification and, optionally, marking include having multiple encoded connector pins or pads located on the needle-side connector which may be conductive or resistive, thus providing encoded identifying means for appropriate detection of the needle. With this construction, the needle can be marked as "used" by breaking (or wiping off) the contact points on the needle-side connector when the needle-side connector is inserted into, or withdrawn from, the device-side connector, or by applying a large destructive current to the encoding pins or pads so as to thereby mark the needle as "used".

Other electrically-based approaches which may be utilized for identification include the detection of currents induced through magnetic fields created by conductive loops or magnetic material molded into, or applied to, the needle-side connector that causes detectable inductive shifts at the device-side connector. With this construction, the needle may also be permanently altered (i.e., so as to mark that it is used) by inducing a destructive current in the needle-side connector. Capacitive techniques can also be employed for identification purposes, with the needle being identified through the capacitive properties of the needle-side connector.

Optical means for identification and, optionally, marking include the use of a light emitting diode (LED) or other light source for optical detection, which may be based on a detection array or on a fluorescence or phosphorescence technique. In addition, the needle-side connector may use a persistent phosphorescent material, illuminated by a LED of suitable wavelength, in order to provide a persistent luminous optical marking that may be detected for a period of time after use.

Mechanical means for identification and, optionally, marking include forming (e.g., by molding) a uniquely-shaped interconnect wherein the needle-side connector must mechanically mate with the device-side connector before the needle can be used, with marking being achieved by physically altering one or the other, or both, of the needle-side connector and the device-side connector during mating or withdrawal.

In one preferred form of the invention, there is provided an interconnect for connecting a needle electrode to a neurological testing device, the interconnect comprising:

a needle-side connector and a device-side connector, wherein the needle-side connector and the device-side connector have complementary aspects so as to ensure that the correct needle electrode is used with a given neurological testing device.

In another preferred form of the invention, there is provided a method for connecting a needle electrode to a neurological testing device, the method comprising:

providing an interconnect comprising a needle-side connector and a device-side connector, wherein the needle-side connector and the device-side connector have complementary aspects so as to ensure that the correct needle electrode is used with a given neurological testing device; and connecting the needle-side connector to the device-side connector.

BRIEF DESCRIPTION OF THE DRAWINGS

These and other objects and features of the present invention will be more fully understood from the following detailed description of the preferred embodiments of the invention, which should be read in conjunction with the accompanying drawings wherein.

DETAILED DESCRIPTION OF THE PREFERRED EMBODIMENTS

The present invention comprises a novel interconnect for connecting a needle electrode to a neurological testing device, wherein the interconnect is configured to determine if the correct needle is being connected to the neurological testing device. The invention preferably also comprises an additional, and supplementary, ability to mark the needle as "used" when a procedure is performed, thereby making it easy to determine when a needle has been previously used.

In one form of the present invention, there is provided a novel interconnect for connecting a needle electrode to a neurological testing device. The novel interconnect comprises a needle-side connector and a mating device-side connector, wherein the needle-side connector and device-side connector have complementary aspects so as to ensure that an appropriate needle electrode is used with an appropriate neurological testing device. Furthermore, the novel interconnect is preferably constructed so that the needle-side connector is marked during use, so as to facilitate determining when the needle electrode has been previously used, whereby to help ensure single use of the needle electrode.

Significantly, the present invention can be implemented using, in a novel fashion, the simple and inexpensive manufacturing techniques commonly employed in manufacturing interconnects for coupling needles to neurological testing devices.

Figure 1:
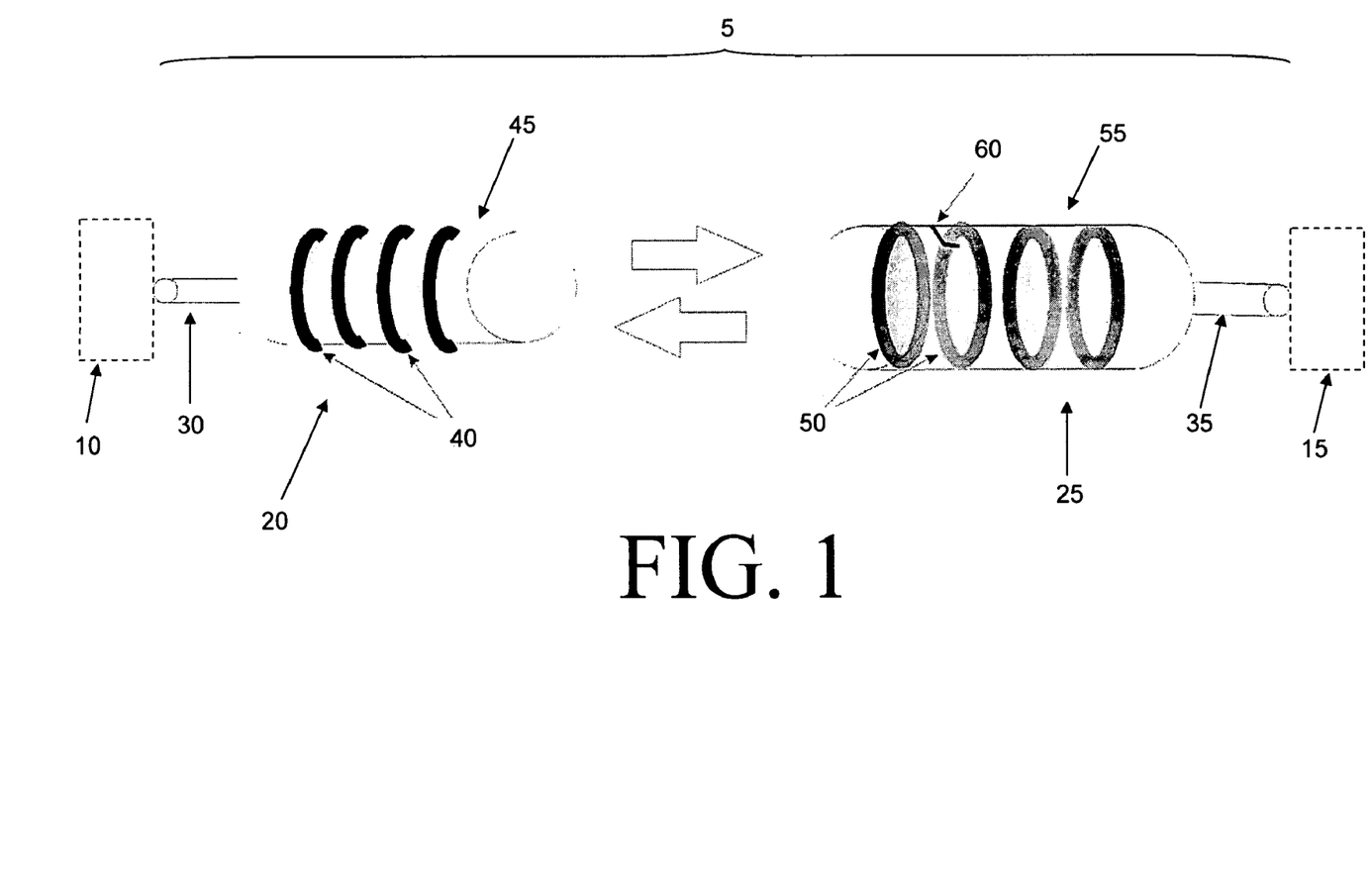
FIG. 1 is a schematic view of a construction in which connector pins or contacts are encoded on the needle-side connector and ensure proper identification of the needle, and further wherein marking occurs by breaking the pins or by wiping the contacts upon disconnection through the use of a spring-loaded hook located on the device-side connector.

Looking now at FIG. 1, there is shown a novel interconnect 5 for connecting a needle electrode 10 to a neurological testing device 15. Interconnect 5 generally comprises a needle-side connector 20 and a mating device-side connector 25, with needle-side connector 20 being connected to needle electrode 10 via a cable 30 and with device-side connector 25 being connected to neurological testing device 15 via a cable 35. In this form of the invention, needle-side connector 20 preferably constitutes a male member and device-side connector 25 preferably constitutes a female member, and electrical means are used to ensure that the correct needle electrode is connected to the neurological testing device.

More particularly, and still looking now at FIG. 1, one or more resistive contact pads 40 are disposed on the outside of the housing 45 of needle-side connector 20. Corresponding contact pads 50 are also provided on the inside of the hollow housing 55 of device-side connector 25. Contact pads 40 on needle-side connector 20 are positionally disposed so that they are effectively "encoded", whereby to uniquely identify needle electrode 10. Contact pads 50 on device-side connector 25 are correspondingly positionally disposed so as to detect when the correct needle electrode is connected to the neurological testing device. In other words, by providing one or more uniquely-disposed contact pads 40 on needle-side connector 20, and by providing one or more correspondingly uniquely-disposed contact pads 50 on device-side connector 25, successful electrical interconnection may be used to confirm that the appropriate needle electrode is connected to the neurological testing device.

With this form of the invention, marking (to ensure that the needle is only used once) occurs upon disconnection. More particularly, device-side connector 25 includes a spring-loaded hook 60 which breaks (or otherwise renders inoperable) one or more of the contact pads 40 on the outside of needle-side connector 20 when needle-side connector 20 is disconnected from device-side connector 25. As a result, if needle electrode 10 were to be thereafter re-used, one or more of contacts pads 40 would be inoperative and it would be impossible to achieve the successful electrical interconnection needed to confirm that an appropriate needle electrode is connected to the neurological testing device.

Thus it will be seen that, in this form of the invention, in order for successful electrical interconnection to be achieved, (i) the needle electrode 10 must be the appropriate needle for neurological testing device 15, and (ii) needle electrode 10 must not have been previously used.

In FIG. 1, contact pads 40, 50 are shown as ring-like structures. However, in an alternative construction, contact pads

40, 50 could comprise smaller "island" pads disposed on needle-side connector 20 and device-side connector 25. In this alternative construction, spring-loaded hook 60 may still be used for marking purposes. Alternatively, the marking function could be implemented by applying a large electrical current to contact pads 40 of needle-side connector 20, thereby "blowing" the conductive or resistive contacts like a fuse, whereby to permanently alter their original state so that the needle can be recognized as "used". It is also possible to form contact pads 40, 50 with other geometries, e.g., as bars, as pins, etc.

Figure 2:
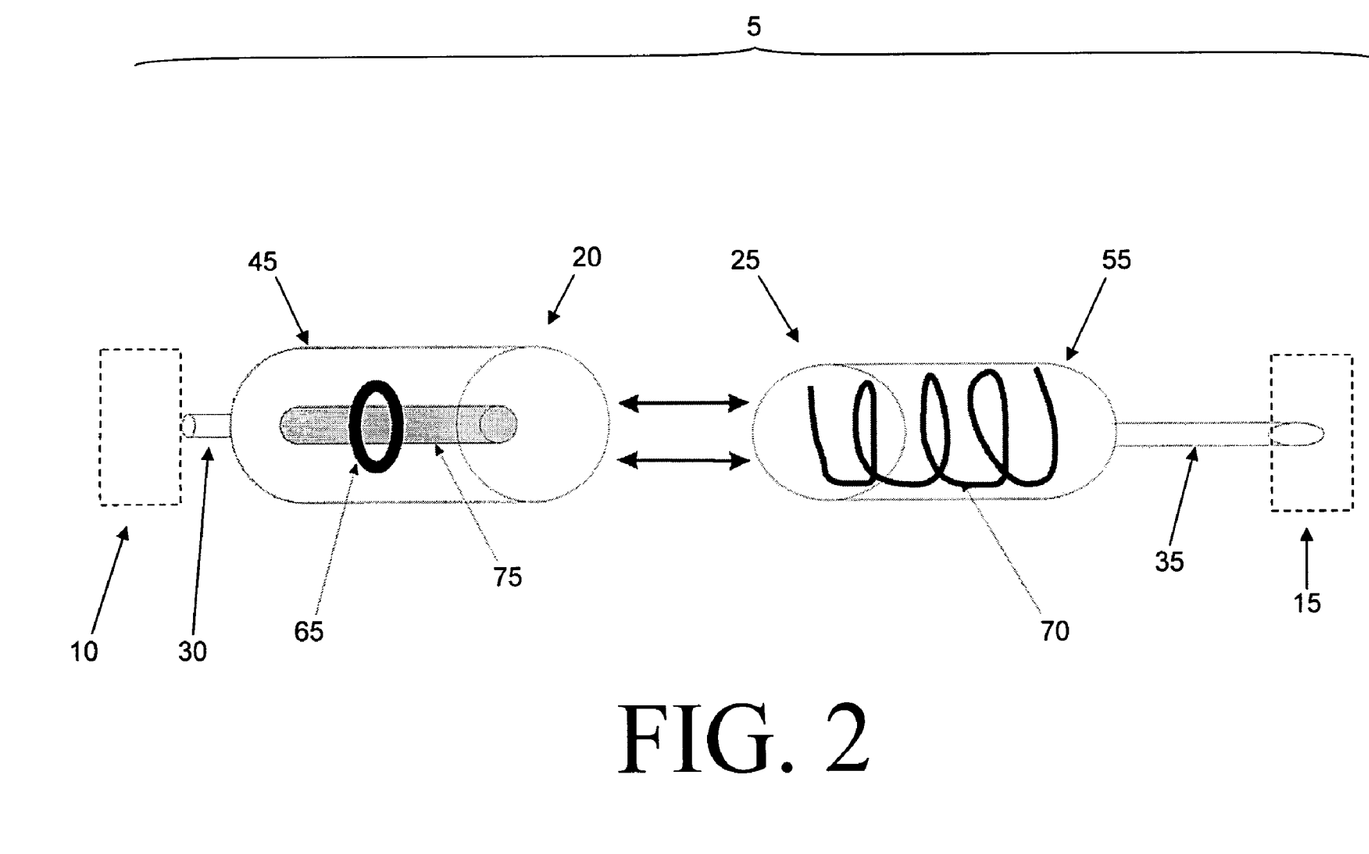
FIG. 2 is a schematic view of a construction in which the needle-side connector is a standard connector fitted with a thin aluminum wire ring on the inside thereof which acts as a secondary transformer winding once a changing current is induced in the wire ring, with the device-side connector holding a multiple-turn wire which acts as the primary transformer winding through which a magnetic field is induced—identification occurs due to the presence of the second transformer winding being low resistance, and one-time usability is ensured by imposing an excessive load on the second transformer winding which results in breaking the secondary wire ring.

Looking next at FIG. 2, there is shown another novel interconnect 5 for connecting needle electrode 10 to neurological testing device 15. Again, interconnect 5 generally comprises needle-side connector 20 and device-side connector 25, with needle-side connector 20 being connected to needle electrode 10 via cable 30 and with device-side connector 25 being connected to neurological testing device 15 via cable 35. In this form of the invention, needle-side connector 20 preferably constitutes a female member and device-side connector 25 preferably constitutes a male member, and electromagnetic means are used to ensure that the correct needle electrode is connected to the neurological testing device.

More particularly, and still looking now at FIG. 2, in this form of the invention, a thin conductive loop 65 is disposed on the interior of housing 45 of needle-side connector 20. Conductive loop 65 may be formed out of substantially any appropriate conductive material, e.g., aluminum, copper alloy, gold or alloys thereof, etc., and is preferably in the range of 0.0005 inches to 0.003 inches thick, depending on the desired conductivity or current-carrying capacity. Conductive loop 65 may comprise a structure formed by vapor deposition, chemical plating, foil tape, wire, or other conventional means well known to those skilled in the art. Device-side connector 25 comprises a coil 70 comprising one or more turns of wire (e.g., copper, aluminum, etc.) wound on the inside of housing 55 of device-side connector 25.

The novel interconnect of FIG. 2 relies on the theory of transformers. More particularly, a transformer is a device that transfers electrical energy from one circuit to another through a shared magnetic field. In the implementation of FIG. 2, the primary circuit of the transformer is wire coil 70 located in device-side connector 25 and to which a voltage is applied. The secondary circuit of the transformer is conductive ring 65 located on needle-side connector 20, where conductive ring 65 represents a shorted turn. Upon mating of needle-side connector 20 with device-side connector 25, the application of a changing current in the primary circuit (i.e., wire coil 70) creates a magnetic field which induces a changing voltage and current in the secondary circuit (i.e., conductive ring 65). Because the secondary circuit (i.e., conductive ring 65) is effectively shorted, the primary circuit (i.e., wire coil 70) must therefore deliver a relatively high current which can be detected (e.g., by neurological testing device 15). It is the presence of this high current that identifies the needle as being the one required to be used by the neurological testing device. By contrast, a conventional "off-the-shelf" needle would not have a conductive ring 65 in its needle-side connector and therefore the conventional "off-the-shelf" needle would not be identified as the needle required to be used by the neurological testing device (and would, hence, be identified as an unqualified needle).

If desired, a ferrite core 75 may be employed in needle-side connector 20 so as to enhance and direct the magnetic field created by the current in wire coil 70.

With the construction shown in FIG. 2, needle-side connector 20 can be marked as "used" in the following manner. When testing for the patient has been completed, a large current is applied to the primary coil (i.e., wire coil 70) by neurological testing device 15. This large current in the primary coil induces a large current in the secondary coil (i.e., conductive ring 65) which causes conductive ring 65 to be destroyed, i.e., in a fuse-like manner. This causes a sudden, detectable reduction in the primary current flowing through the primary coil (i.e., wire coil 70). Thus, the destructive current passing through conductive ring 65 "marks" needle-side connector 20 so that it is easy to determine when a needle has been previously used.

If desired, a laser cutting process may be used to modify the width of conductive ring 65 in order to control the level of current required to break the secondary loop (i.e., conductive ring 65). Thus, where destructive marking is to be used, device-side connector 25 (which includes wire coil 70) constitutes a re-usable, multi-purpose connector, while the needle-side connector (which includes conductive ring 65) constitutes a single-use, disposable connector.

The construction shown in FIG. 2 may be modified so that needle-side connector 20 has two conductive rings 65 instead of one, in which case the needle-side connector has two conductive secondary loops. In this two-ring construction, one conductive ring could be destroyed by current overload so as to achieve the desired needle marking, while the other conductive ring could stay intact in order to continue to detect the attachment of the needle-side connector to the device-side connector. Furthermore, if desired, a visible indicator may be provided on needle-side connector 20 to show that the conductive ring has been destroyed—in this case, the visible indicator might comprise a discoloration of a specific area of the connector housing that discolors when the conductive ring is electrically opened by the electrical current overload.

The construction shown in FIG. 2 may also be modified so that it uses magnetic material that is applied to, or is molded into, needle-side connector 20. In this form of the invention, a magnetic material such as a high permeability (μ) powder (available from Fermag Technologies of New Jersey or Unimagnet Industry Co., Ltd of China) is applied to the surface of, or is molded into, the plastic housing of needle-side connector 20. Alternatively, a high permeability foil or formed magnetic core material (available from Ferronics, Inc. of New York) can be incorporated into the housing of needle-side connector 20. Again, wire coil 70 on device-side connector 25 is excited by a voltage. The induced current is a function of the characteristics of the coil—size, number of turns, etc. When the needle-side connector, with the high permeability material in its housing, is inserted into the magnetic field of wire coil 70, the inductance of the coil will increase, causing a detectable change in the primary excitation current. This change in the primary excitation current identifies the needle-side connector, so as to ensure that the correct needle is used with the neurological testing device. By contrast, a conventional "off-the-shelf" needle would not have this high permeability magnetic material in its needle-side connector, and would therefore be identified by the neurological testing device as an inappropriate needle which should not be used.

Figure 3:
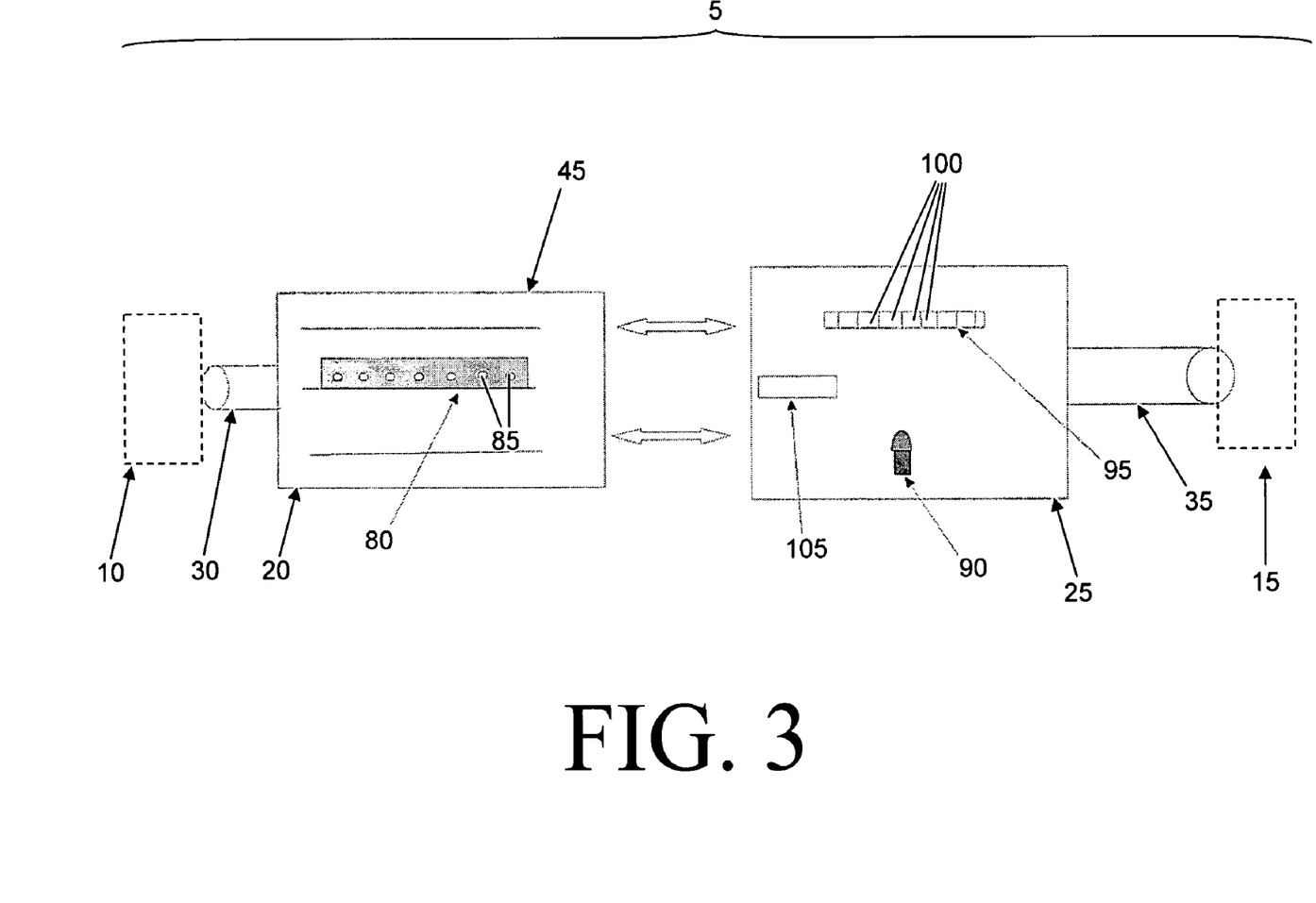
FIGS. 3 and 4 are schematic views of a construction in which the needle-side connector contains a molded plastic piece with a physical pattern thereon which is specific to the model of the needle, and the device-side connector contains a small LED on one side and a detector array on the other side—when the two connectors are joined, identification occurs when the detector array detects the light pattern created by the LED and the molded plastic piece and then converts the detected light pattern into appropriate electrical signals, and one-time usability of the needle is ensured when a spring-loaded blade attached to the device-side connector scrapes off (or otherwise physically alters) the molded plastic piece on the needle-side connector.
Figure 4:
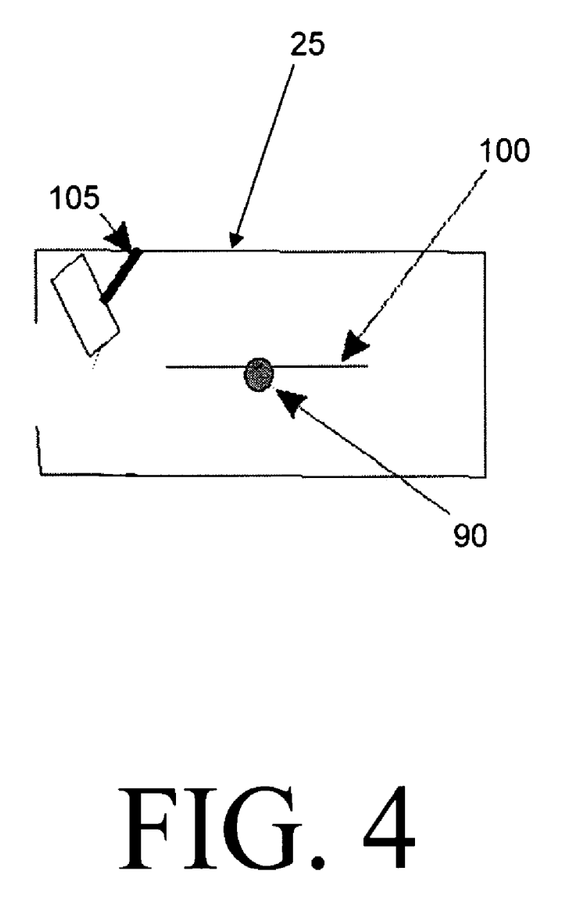

Looking next at FIGS. 3 and 4, there is shown another novel interconnect 5 for connecting needle electrode 10 to neurological testing device 15. Again, interconnect 5 generally comprises needle-side connector 20 and device-side connector 25, with needle-side connector 20 being connected to needle electrode 10 via cable 30 and with device-side connector 25 being connected to neurological testing device 15 via cable 35. In this form of the invention, needle-side connector 20 preferably constitutes a male member and device-side connector 25 preferably constitutes a female member, and optical means are used to ensure that the appropriate needle electrode is connected to the neurological testing device.

More particularly, and still looking now at FIGS. 3 and 4, in this form of the invention, needle-side connector 20 has a light-altering element 80 (e.g., made of molded plastic) disposed within housing 45. Light-altering element 80 preferably comprises a distinct pattern of holes or bumps or recesses or masks or other structures 85 which can modify light falling on light-altering element 80. More particularly, in one form of the invention, light-altering element 80 is opaque and holes 85 are provided. In another form of the invention, light-altering element 80 comprises a light-passing body, and bumps or recesses or masks or other structures 85 comprise substantially any surface configuration which can alter the light passing through the element. Device-side connector 25 houses an LED (or other light source) 90 on one side of the connector and a detector array 95 on the other side of the connector. Detector array 95 comprises a plurality of detector cells 100. When needle-side connector 20 is mated with device-side connector 25, LED 90 illuminates light-altering element 80 (and its holes or bumps or recesses or masks or other structures 85) so that a distinct pattern of light falls on detector array 95. Detector array 95 then provides an output signal which corresponds to the pattern of light falling on detector array 95. If this pattern of light is consistent with the pattern of light established by a "correct" needle, then it will be known that the correct needle is connected to neurological testing device 15. On the other hand, if the pattern of light falling on detector array 95 is not consistent with the pattern of light established by a "correct" needle, then it will be known that an unqualified needle is connected to neurological testing device 15.

The use of multiple holes or bumps or recesses or masks or other structures 85 on light-altering element 80, and the use of multiple detectors cells 100 on detector array 95, makes it possible to encode various information about the needle (such as type, length, gauge and the like) on needle-side connector 20. This provides a unique means for identifying the needle.

For marking purposes, at the time that needle-side connector 20 is disconnected from device-side connector 25, a spring-loaded blade 105 (or other mechanical element) engages and scores light-altering element 80, disrupting any future identification process, whereby to mark the needle to show that it has been previously used.

Thus it will be seen that, in this form of the invention, in order for detection array 95 to output a signal indicating that the needle is satisfactory, (i) needle electrode 10 must be the appropriate needle for the neurological testing device 15, and (ii) needle electrode 10 must not have been previously used.

Figure 5:
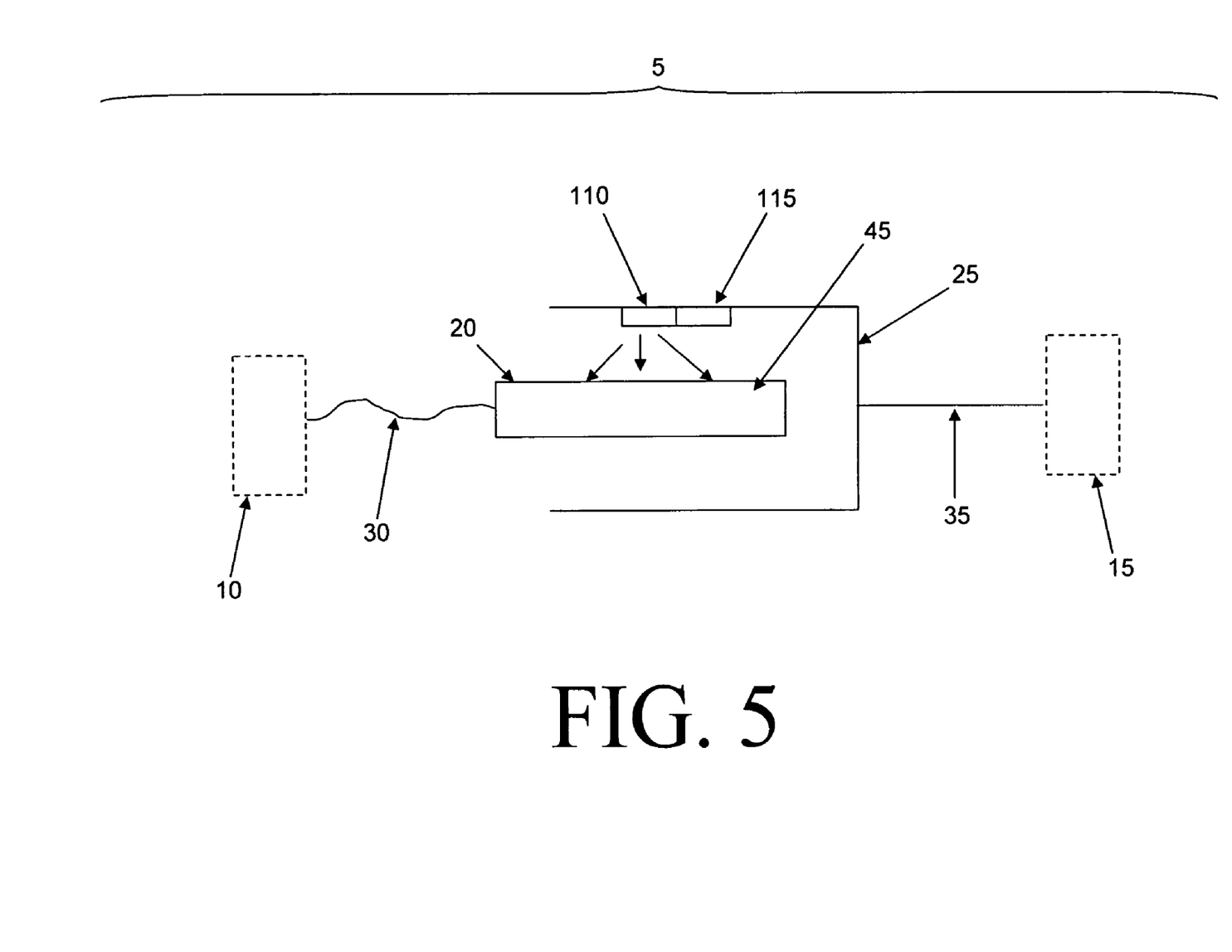
FIGS. 5 and 6 are schematic views of a construction which uses fluorescence or phosphorescence for needle identification.
Figure 6:
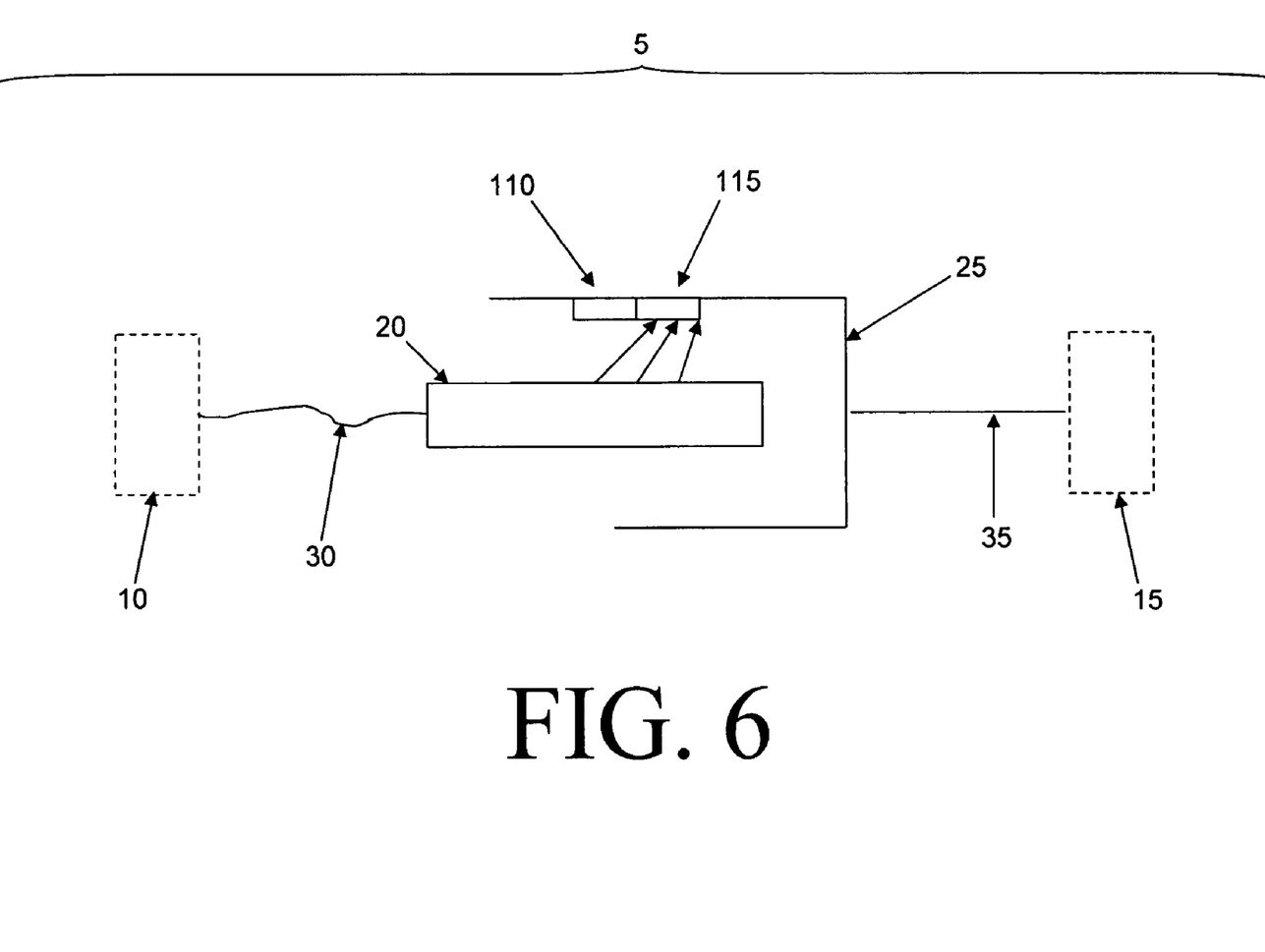

Looking next at FIGS. 5 and 6, there is shown another novel interconnect 5 for connecting needle electrode 10 to neurological testing device 15. Again, interconnect 5 generally comprises needle-side connector 20 and device-side connector 25, with needle-side connector 20 being connected to needle electrode 10 via cable 30 and with device-side connector 25 being connected to neurological testing device 15 via cable 35. In this form of the invention, needle-side connector 20 constitutes a male member and device-side connector 25 constitutes a female member, and fluorescence or phosphorescence is used to ensure that the appropriate needle electrode is connected to the neurological testing device.

More particularly, and still looking now at FIGS. 5 and 6, in this form of the invention, needle-side connector 20 may be coated with, or have embedded in its housing 45, a fluorescent or phosphorescent material such as are supplied by Shannon Luminous Materials, Inc. of California or Sunshow Photoluminescent Pigment Co., Ltd of China. This fluorescent or phosphorescent material fluoresces or phosphoresces when illuminated by an LED 110 (or other light source of suitable wavelength to cause fluorescence or phosphorescence) mounted to the interior of the device-side connector 25. These fluorescent or phosphorescent materials are generically zinc sulfide:Copper (ZnS:Cu) or rare earth aluminate ($Al_2O_3$:Eu) compounds that are readily known to those skilled in the art, and are widely commercially available. A photodetector 115 mounted to the interior of the device-side connector 25 receives the fluorescent or phosphorescent light that is emitted by the fluorescent or phosphorescent material on needle-side connector 20 in response to the LED illumination.

Preferably, the LED 110 (or other illumination source that contains a wavelength or wavelengths that will excite the materials) is pulsed "on" for a number of milliseconds so as to stimulate the material while the photodetector 115 is "off". Photodetector 115 is then turned "on" after LED 110 is turned "off". This approach ensures that the light received by photodetector 115 emanates from the fluorescent or phosphorescent material of the needle-side connector rather than from LED 110. It is the fluorescence or phosphorescence emanating from a needle-side connector 20 which identifies the needle as the one which is required to be used with neurological testing device 15. By contrast, a conventional "off-the-shelf" needle would not have the fluorescent or phosphorescent material in the needle-side connector and hence would fail to produce the required fluorescence or phosphorescence, so that it would be identified by the neurological testing device as an unqualified needle.

One or more areas of the needle-side connector may contain the fluorescent or phosphorescent material so as to permit the encoding of information about the needle (such as type, length, gauge and the like).

Marking can be achieved through the use of a long persistence phosphorescent material (and an LED of appropriate wavelength spectra to cause phosphorescence of the material). More particularly, in this case, by using long persistence phosphorescent material, the persistent luminous optical marking can be detected for a period of time after use, thereby providing a means to determine that the needle has already been used.

Figure 7:
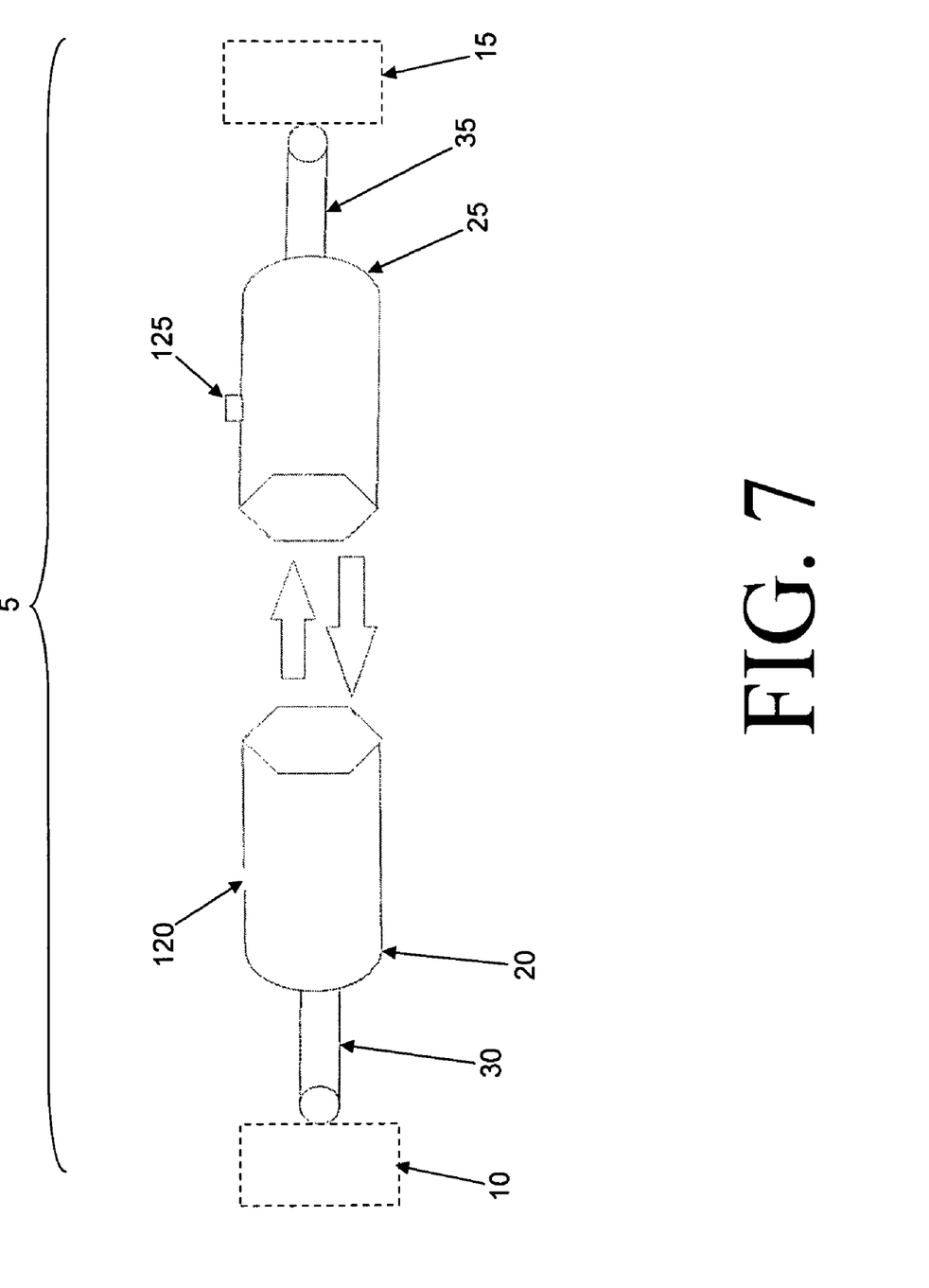
FIG. 7 is a schematic view showing the construction details of a molded, unique plastic needle-side connector and corresponding device-side connector, wherein the unique mechanical structure of the two interconnect components ensures proper needle identification, and further wherein a spring blade is provided to break off a portion of a connector, thereby ensuring one-time usability of the needle.

Looking next at FIG. 7, there is shown another novel interconnect 5 for connecting needle electrode 10 to neurological testing device 15. Again, interconnect 5 generally comprises needle-side connector 20 and device-side connector 25, with needle-side connector 20 being connected to needle electrode 10 via cable 30 and with device-side connector 25 being connected to neurological testing device 15 via cable 35. In this form of the invention, needle-side connector 20 preferably constitutes a female member and device-side connector 25 preferably constitutes a male member, and mechanical interlocking is used to ensure that the appropriate needle electrode is connected to the neurological testing device.

More particularly, and still looking now at FIG. 7, in this form of the invention, needle-side connector 20 has a unique mechanical design featuring a hexagonal (or any other uniquely shaped) end that connects to a correspondingly-configured device-side connector 25. Needle-side connector 20 has a small hole 120 (cut by laser or with a punch, etc.). Device-side connector 25 has a matching hexagonal (or any other uniquely shaped) end that fits snugly into needle-side connector 20 and has a protruding plastic molded tab 125 that uniquely fits, and therefore closes, the connection to the open hole 120 on needle-side connector 20.

Marking may be achieved when the small tab 125 on device-side connector 25 is broken off during detachment.

Alternatively, the open hole 120 could be provided on device-side connector 25 and the protruding plastic molded tab 125 could be provided on needle-side connector 20, etc.

MODIFICATIONS

While the foregoing invention has been described with reference to its preferred embodiments, various alterations and modifications will occur to those skilled in the art in view of the present disclosure. All such alterations and modifications are intended to fall within the scope of the invention.

What is claimed is:

1. An interconnect for connecting a needle electrode to a neurological testing device, the interconnect comprising:
    a needle-side connector and a device-side connector, wherein the needle-side connector and the device-side connector have complementary aspects so as to ensure that the correct needle electrode is used with a given neurological testing device;
    wherein the complementary aspects are embodied in at least one from the group consisting of electrical apparatus, optical apparatus and mechanical apparatus;
    wherein the optical apparatus comprises a fluorescent or phosphorescent element disposed on the needle-side connector, and a light source and a light detector disposed on the device-side connector; and
    wherein fluorescence or phosphorescence emanating from the needle-side connector and detected by the light detector disposed on the device-side connector identifies the needle electrode as one which may be used with the given neurological testing device.

2. The interconnect according to claim 1 wherein the electrical apparatus comprises at least one electrical contact disposed on the needle-side connector and at least one corresponding electrical contact disposed on the device-side connector.

3. The interconnect according to claim 2 wherein a plurality of electrical contacts are disposed on the needle-side connector and a plurality of corresponding electrical contacts are disposed on the device-side connector, and further wherein the plurality of electrical contacts are configured so as to encode characteristics of the needle electrode.

4. The interconnect according to claim 2 wherein the interconnect is constructed so that the needle-side connector is marked during use.

5. The interconnect according to claim 4 wherein the needle-side connector is marked by providing an element on the device-side connector for rendering inoperative the at least one electrical contact disposed on the needle-side connector.

6. The interconnect according to claim 1 wherein the electrical apparatus comprises at least one conductive loop disposed on the needle-side connector and at least one conductive coil disposed on the device-side connector.

7. The interconnect according to claim 6 wherein two conductive loops are disposed on the needle-side connector.

8. The interconnect according to claim 6 wherein a conductive core extends through the at least one conductive loop.

9. The interconnect according to claim 6 wherein the interconnect is constructed so that the needle-side connector is marked during use.

10. The interconnect according to claim 9 wherein the needle-side connector is marked by rendering inoperative the at least one conductive loop disposed on the needle-side connector.

11. The interconnect according to claim 10 wherein the at least one conductive loop is rendered inoperative by inducing a destructive current through the at least one conductive loop.

12. The A interconnect according to claim 1 wherein the electrical apparatus comprises magnetic material which is disposed on the needle-side connector and at least one conductive coil disposed on the device-side connector.

13. The interconnect according to claim 1 wherein the optical apparatus comprises a light-altering element disposed on the needle-side connector, and a light source and a light detector disposed on the device-side connector.

14. The interconnect according to claim 13 wherein the light source comprises an LED.

15. The interconnect according to claim 13 wherein the light-altering element comprises an opaque body having at least one opening therein.

16. The interconnect according to claim 15 wherein the opaque body has a plurality of openings therein, and further wherein the plurality of openings are formed so as to encode needle characteristics.

17. The interconnect according to claim 13 wherein the light-altering element comprises a light-passing body having at least one light-modifying structure thereon.

18. The interconnect according to claim 17 wherein the light-passing body has a plurality of bumps formed thereon, and further wherein the plurality of bumps are formed so as to encode needle characteristics.

19. The interconnect according to claim 13 wherein the interconnect is constructed so that the needle-side connector is marked during use.

20. The interconnect according to claim 19 wherein the light-modifying structure comprises at least one from the group consisting of a bump, a recess and a mask.

21. The interconnect according to claim 19 wherein the needle-side connector is marked by mechanically altering the light-altering element disposed on the needle-side connector.

22. The interconnect according to claim 1 wherein the interconnect is constructed so that the needle-side connector is marked during use.

23. The interconnect according to claim 1 wherein the needle-side connector is optically marked during use.

24. The interconnect according to claim 1 wherein the mechanical apparatus comprises forming the needle-side connector with a first configuration and forming the device-side connector with a second configuration.

25. The interconnect according to claim 24 wherein the interconnect is constructed so that the needle-side connector is marked during use.

26. The interconnect according to claim 25 wherein the needle-side connector is marked by mechanically modifying the needle-side connector during use.

27. A method for connecting a needle electrode to a neurological testing device, the method comprising:
    providing an interconnect comprising a needle-side connector and a device-side connector, wherein the needle-side connector and the device-side connector have complementary aspects so as to ensure that the correct needle electrode is used with a given neurological testing device;
    wherein the complementary aspects are embodied in at least one from the group consisting of electrical apparatus, optical apparatus and mechanical apparatus;
    wherein the optical apparatus comprises a fluorescent or phosphorescent element disposed on the needle-side connector, and a light source and a light detector disposed on the device-side connector;

wherein fluorescence or phosphorescence emanating from the needle-side connector and detected by the light detector disposed on the device-side connector identifies the needle electrode as one which may be used with the given neurological testing device; and connecting the needle-side connector to the device-side connector.

28. The method according to claim 27 wherein the electrical apparatus comprises at least one electrical contact disposed on the needle-side connector and at least one corresponding electrical contact disposed on the device-side connector.

29. The method according to claim 28 wherein a plurality of electrical contacts are disposed on the needle-side connector and a plurality of corresponding electrical contacts are disposed on the device-side connector, and further wherein the plurality of electrical contacts are configured so as to encode characteristics of the needle electrode.

30. The method according to claim 28 wherein the interconnect is constructed so that the needle-side connector is marked during use.

31. The method according to claim 30 wherein the needle-side connector is marked by providing an element on the device-side connector for rendering inoperative the at least one electrical contact disposed on the needle-side connector.

32. The method according to claim 27 wherein the electrical apparatus comprises at least one conductive loop disposed on the needle-side connector and at least one conductive coil disposed on the device-side connector.

33. The method according to claim 32 wherein two conductive loops are disposed on the needle-side connector.

34. The method according to claim 32 wherein the interconnect is constructed so that the needle-side connector is marked during use.

35. The method according to claim 34 wherein the needle-side connector is marked by rendering inoperative the at least one conductive loop disposed on the needle-side connector.

36. The method according to claim 35 wherein the at least one conductive loop is rendered inoperative by inducing a destructive current through the at least one conductive loop.

37. The method according to claim 27 wherein the electrical apparatus comprises magnetic material which is disposed on the needle-side connector and at least one conductive coil disposed on the device-side connector.

38. The method according to claim 27 wherein the optical apparatus comprises a light-altering element disposed on the needle-side connector, and a light source and a light detector disposed on the device-side connector.

39. The method according to claim 38 wherein the light-altering element comprises an opaque body having at least one opening therein.

40. The method according to claim 39 wherein the opaque body has a plurality of openings therein, and further wherein the plurality of openings are formed so as to encode needle characteristics.

41. The method according to claim 38 wherein the light-altering element comprises a light-passing body having at least one light-modifying structure thereon.

42. The method according to claim 38 wherein the interconnect is constructed so that the needle-side connector is marked during use.

43. The method according to claim 42 wherein the light-modifying structure comprises at least one from the group consisting of a bump, a recess and a mask.

44. The method according to claim 42 wherein the needle-side connector is marked by mechanically altering the light-altering element disposed on the needle-side connector.

45. The method according to claim 27 wherein the interconnect is constructed so that the needle-side connector is marked during use.

46. The method according to claim 27 wherein the needle-side connector is optically marked during use.

* * * * *